United States Patent
Sato et al.

(10) Patent No.: US 6,344,299 B1
(45) Date of Patent: Feb. 5, 2002

(54) PHOTOPOLYMERIZATION INITIATOR, PHOTOPOLYMERIZABLE INITIATOR COMPOSITION, COLOR FILTER AND LIQUID CRYSTAL DISPLAY

(75) Inventors: Hiroyuki Sato; Takanori Fukumura; Fumitaka Ooizumi, all of Yokohama; Takashi Kato, Ichihara, all of (JP)

(73) Assignee: Chisso Corporation, Osaka (JP)

(*) Notice: Subject to any disclaimer, the term of this patent is extended or adjusted under 35 U.S.C. 154(b) by 0 days.

(21) Appl. No.: 09/440,702

(22) Filed: Nov. 16, 1999

(30) Foreign Application Priority Data

Nov. 30, 1998 (JP) .................................. 10-339915

(51) Int. Cl.$^7$ .................... G02F 1/1335; C07C 409/38; C07C 409/40; C08F 4/36
(52) U.S. Cl. .................... 430/7; 430/270.1; 430/281.1; 522/13; 522/24; 522/46; 560/302; 349/106
(58) Field of Search ................. 560/302; 430/7, 430/270.1, 281.1; 349/106; 522/13, 46, 24

(56) References Cited

U.S. PATENT DOCUMENTS

| | | | |
|---|---|---|---|
| 4,171,252 A | 10/1979 | Fantazier | |
| 4,416,826 A | 11/1983 | Neckers | |
| 4,752,649 A | 6/1988 | Neckers | |

FOREIGN PATENT DOCUMENTS

| | | | |
|---|---|---|---|
| DE | 1694149 | 11/1968 | |
| JP | 3-60322 | 9/1991 | |
| JP | 6-348010 A | * 12/1994 | |
| JP | 10-17547 | 1/1998 | |
| JP | 10-045927 A | * 2/1998 | |
| JP | 10-208542 A | * 8/1998 | |

OTHER PUBLICATIONS

"Photochemistry of Perester Initiators", by Thijs et al., J. Org. Chem., vol. 44, No. 23, 1979, pp. 4123–4128.
"Photoinitiated Polymerization of Vinyl Monomers by Benzophenone t–Butyl Peresters", by Abu–Abdoun et al., Journal of Polymer Science: Polymer Chemistry Edition, vol. 21, 1983, pp. 3129–3144.

* cited by examiner

Primary Examiner—John A. McPherson
(74) Attorney, Agent, or Firm—McDermott, Will & Emery

(57) ABSTRACT

Provided is a photopolymerization initiator which has a high sensitivity and is inexpensive and which does not cause precipitation of crystals when kept in cold storage after diluted and dissolved in an organic solvent. The photopolymerization initiator comprises a structure represented by the following Formula (1):

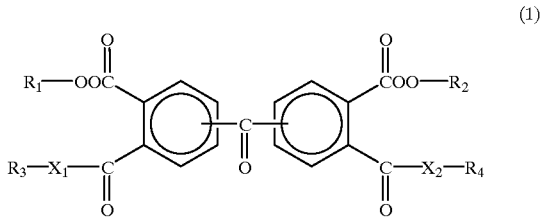

(1)

14 Claims, 1 Drawing Sheet

PHOTOPOLYMERIZATION INITIATOR, PHOTOPOLYMERIZABLE INITIATOR COMPOSITION, COLOR FILTER AND LIQUID CRYSTAL DISPLAY

FIELD OF THE INVENTION

The present invention relates to a photopolymerization initiator, a photopolymerizable initiator composition, a photosensitive colored composition for producing a color filter used in a color liquid crystal display element and a color solid image pickup element, and a color filter and a liquid crystal display element using the same.

BACKGROUND OF THE INVENTION

A polymerization method in which light is applied in the presence of a photopolymerization initiator when a monomer or oligomer having a polymerizable unsaturated group such as a vinyl group is polymerized to cure the paint film has the advantages that the curing speed is fast as compared with those in other methods and curing at a low temperature is possible, and therefore it is widely used for paints and resists. The curing speed depends on a photopolymerization initiator, and therefore various photopolymerization initiators have so far been developed.

German Patent 1694149, for example, discloses benzoin ethers. In addition thereto, photo radical-generating agents such as allyl diazonium salts and halogenated hydrocarbons are known. Further, it is known that certain organic peroxides are useful as a photopolymerization initiator, and that a lot of investigations on these polymerization systems have been made. Specifically, aromatic compounds having a specific t-butyl peroxyester are disclosed in U.S. Pat. Nos. 4,171,252, 4,416,826 and 4,752,649.

Further, synthesis of benzophenone derivatives having one to two peracid esters, such as 4,4'-di(t-butyl peroxycarbonyl)benzophenone and polymerization of vinyl monomers are investigated in Journal of Organic Chemistry, vol. 44, p. 4123 (1979) and Journal of Polymer Science Chemistry, vol. 21, p. 3129 (1983).

Among these compounds, however, those having one peracid ester have had the defect that the photopolymerization activity is low, while those having two peracid esters have had the defects that crystals are liable to precipitate during cold storage after being diluted and dissolved in organic solvents and that the raw materials are expensive and the production cost is high.

A benzophenone derivative having four peracid esters, disclosed in Japanese Patent Publication No. 60322/1991, has a good photopolymerization activity and is inexpensive in terms of a raw material, but it has the defect that crystals precipitate during cold storage after being diluted and dissolved in an organic solvent.

Further, peracid esters disclosed in Japanese Patent Application Laid-Open No. 17547/1998 have a high sensitivity and do not precipitate as crystals while they are kept in cold storage after being diluted and dissolved in an organic solvent. However, they are defective in that the production process is long and involves reactions difficult to carry out, thus leading to a high production cost.

SUMMARY OF THE INVENTION

As described above in detail, an object of the present invention is to provide a photopolymerization initiator which has a high sensitivity and is inexpensive and in which precipitation of crystals does not occur when kept in cold storage after being diluted and dissolved in an organic solvent.

A further object of the invention is to provide a photopolymerizable initiator composition using this photopolymerization initiator, a photosensitive color composition and a color filter.

That is, the first aspect of the present invention is a photopolymerization initiator represented by the following Formula (1):

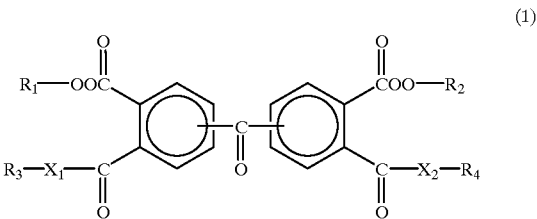

wherein $R_1$ and $R_2$ represent independently a tertiary alkyl group having 4 to 15 carbon atoms or a tertiary aralkyl group having 9 to 15 carbon atoms; $X_1$ and $X_2$ represent independently —O— or —NH—; $R_3$ represents an organic group having 1 to 30 carbon atoms in which an atom bonded to $X_1$ is not an oxygen atom; and $R_4$ represents an organic group having 1 to 30 carbon atoms in which an atom bonded to $X_2$ is not an oxygen atom, a tertiary alkoxy group having 4 to 15 carbon atoms or a tertiary aralkyloxy group having 9 to 15 carbon atoms.

The preferred embodiment is a case where $-X_1-R_3$ and $-X_2-R_4$ in Formula (1) represent independently an alkoxy group which is an alcohol residue of methanol, ethanol, 2-propanol, 1-butanol or benzyl alcohol, a case where they represent independently an alkoxy group which is an alcohol residue of 2-hydroxyethyl (meth)acrylate, 2-hydroxypropyl (meth)acrylate, polyethylene glycol mono(meth)acrylate, polypropylene glycol mono(meth)acrylate or hydroxybutyl (meth)acrylate or a case where they represent independently an alkoxy group which is an alcohol residue of dimethylaminoethanol or diethylaminoethanol.

The second aspect of the invention is a photopolymerization initiator represented by the following Formula (2):

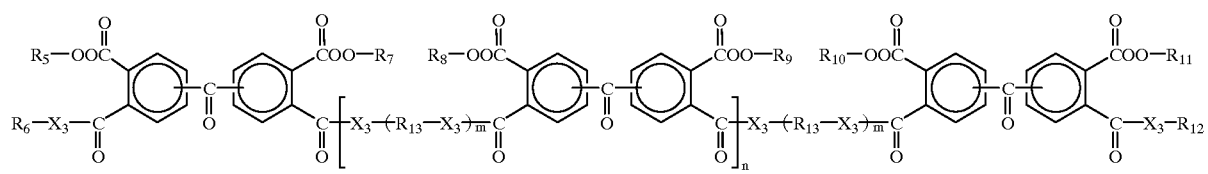

wherein $R_5$, $R_7$, $R_8$, $R_9$, $R_{10}$ and $R_{11}$ represent independently a tertiary alkyl group having 4 to 15 carbon atoms or a tertiary aralkyl group having 9 to 15 carbon atoms; $R_6$ and $R_{12}$ represent independently a tertiary alkoxy group having 4 to 15 carbon atoms, a tertiary aralkyloxy group having 9 to 15 carbon atoms or an organic group having 1 to 30 carbon atoms in which an atom bonded to $X_3$ is not an oxygen atom; $X_3$ represents —O— or —NH—; $R_{13}$ represents an alkylene group having 2 to 8 carbon atoms; m represents an integer of 1 to 30; and n represents an integer of 0 to 30.

The preferred embodiment is a case where $-X_3-R_6$ and $-X_3-R_{12}$ in Formula (2) represent independently an alkoxy group which is an alcohol residue of methanol, ethanol, 2-propanol, 1-butanol or benzyl alcohol, a case where they represent independently an alkoxy group which is an alcohol residue of 2-hydroxyethyl (meth)acrylate, 2-hydroxypropyl (meth)acrylate, polyethylene glycol mono(meth)acrylate, polypropylene glycol mono(meth)acrylate or hydroxybutyl (meth)acrylate or a case where they represent independently an alkoxy group which is an alcohol residue of dimethylaminoethanol or diethylaminoethanol.

The third aspect of the invention is a photopolymerizable initiator composition comprising at least one photopolymerization initiator represented by Formula (1) or (2).

The fourth aspect of the invention is the photopolymerizable initiator composition described above in which at least one photopolymerization initiator other than those represented by Formulas (1) and (2) and/or at least one sensitizing dye is used in an amount of 1 to 80% by weight (hereinafter all percentages are in terms of % by weight) based on the total amount of the photopolymerization initiator(s) or the sensitizing dye(s). A preferred amount is 10 to 70%.

The fifth aspect of the invention is a photosensitive colored composition comprising the photopolymerizable initiator composition of the third invention in admixture with a coloring material.

The sixth aspect of the invention is a color filter produced by using the photosensitive colored composition described above.

The seventh aspect of the invention is a liquid crystal display element produced by using the color filter described above.

DETAILED DESCRIPTION OF THE INVENTION

Figure 1:
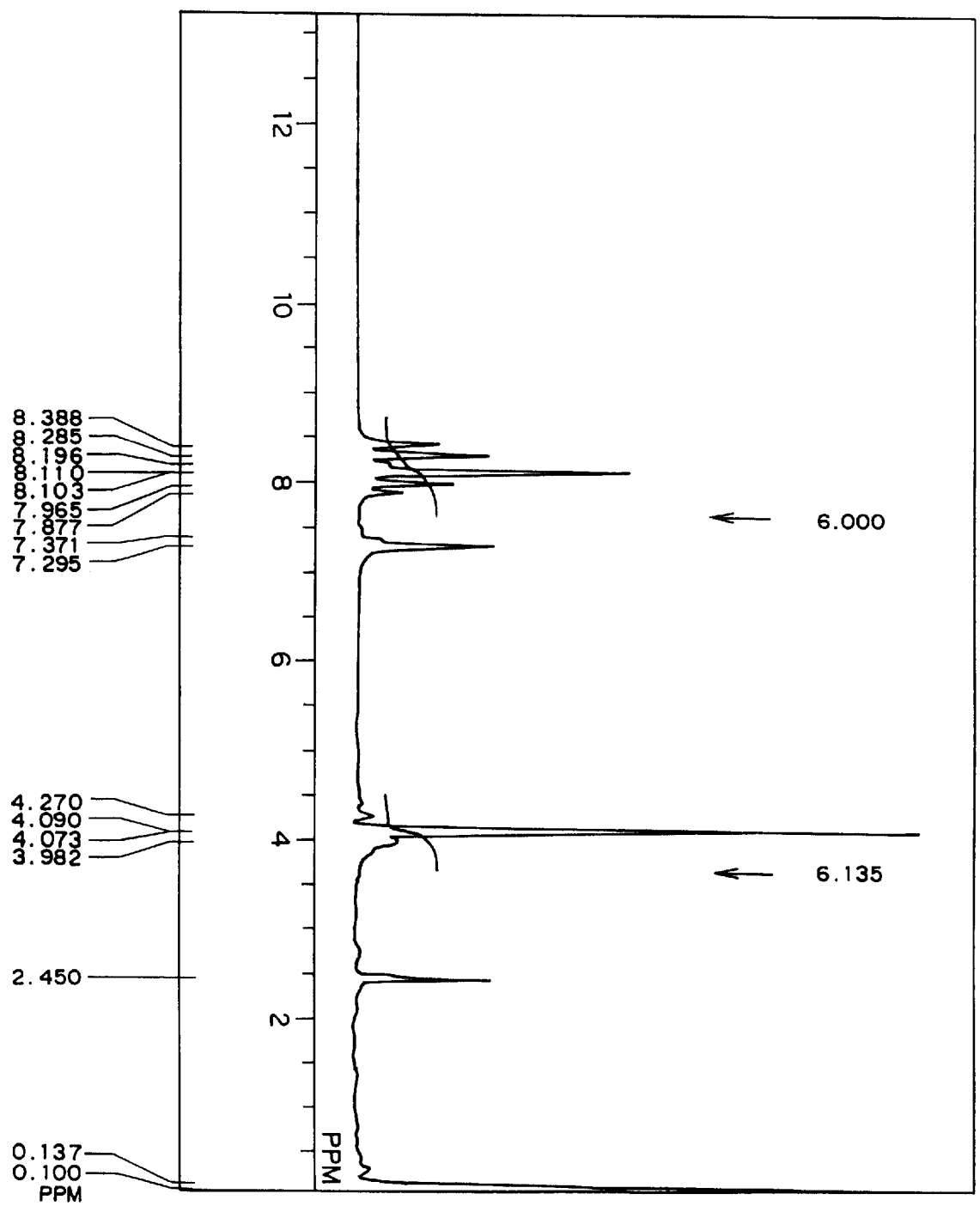
FIG. 1 is a proton NMR chart of a compound obtained by methoxylating 3,3',4,4'-benzophenonetetra-carboxylic dianhydride and chlorinating the carboxylic acids.

The compound represented by Formula (1) according to the present invention can be obtained by reacting tetracarboxylic dianhydride having a benzophenone structure, for example, 3,3',4,4'-benzophenonetetracarboxylic dianhydride with a primary amine or reacting it with a primary alcohol, a secondary alcohol or phenols in the presence of a tertiary amine such as pyridine or triethylamine to form a carboxyl group-containing amide compound or a carboxyl group-containing ester compound, converting the carboxyl groups in the resulting compound into carboxylic chloride with thionyl chloride, phosphorus pentachloride or phosgene and then reacting it with hydroxyperoxide in the presence of a basic compound such as sodium hydroxide, triethylamine or pyridine.

Primary amines, primary alcohols, secondary alcohols and phenols used in the present invention include methylamine, ethylamine, n-propylamine, isopropylamine, n-butylamine, iso-butylamine, sec-butylamine, tert-butylamine, 1-(2-aminoethyl)-2-pyrrolidone, methanol, ethanol, 1-propanol, 2-propanol, 1-butanol, 2-butanol, 1-pentanol, 2-pentanol, 1-hexanol, 2-hexanol, cyclohexanol, 2-ethylhexyl alcohol, octyl alcohol, lauryl alcohol, stearyl alcohol, 1-(2-hydroxyethyl)-2-pyrrolidone, 3-cyclohexene-1-methanol, phenol, 2-hydroxyethyl (meth)acrylate, 2-hydroxypropyl (meth)acrylate, polyethylene glycol mono (meth)acrylate, polypropylene glycol mono(meth)acrylate, hydroxybutyl (meth)acrylate, furfuryl alcohol, tetrahydrofurfuryl alcohol, a compound obtained by modifying tetrahydrofurfuryl alcohol with ε-caprolactone, benzyl alcohol, dimethylaminoethanol and diethylaminoethanol.

From the viewpoint of the production cost, methanol, ethanol, 2-propanol, 1-butanol and benzyl alcohol are particularly preferred since they are inexpensive. From the viewpoint of the sensitivity of the photopolymerization initiator, particularly preferred are 2-hydroxyethyl (meth) acrylate, 2-hydroxypropyl (meth)acrylate, polyethylene glycol mono(meth)acrylate, polypropylene glycol mono(meth) acrylate and hydroxybutyl (meth)acrylate, because peracid ester comes close to the (meth)acryloyl group, so that the resulting compound has improved efficiency as a polymerization initiator.

Further, when dimethylaminoethanol or diethylaminoethanol is used, the sensitivity is enhanced by the effect of amine. From the viewpoint of the developing characteristics of the photopolymerizable initiator composition, tetrahydrofurfuryl alcohol and a compound obtained by modifying tetrahydrofurfuryl alcohol with ε-caprolactone are particularly preferred since the pattern form in developing is good. In this case, included are a hydroxyl group-containing compound formed by an addition reaction of hydrogen contained in alcohol to ε-caprolactone and a compound formed by the same addition reaction of the above compound to ε-caprolactone. In $R_3$ or $R_4$, however, the number of carbon atoms is restricted up to 30.

Hydroperoxides to be reacted with acid chloride include t-butyl hydroperoxide, t-amyl hydroperoxide, t-hexyl hydroperoxide, t-octyl hydroperoxide and t-cumyl hydroperoxide. From the viewpoint of the production cost, t-butyl hydroperoxide is particularly preferred.

The compound represented by Formula (2) according to the present invention can be obtained by reacting tetracarboxylic dianhydride having a benzophenone structure, for example, 3,3',4,4'-benzophenonetetracarboxylic dianhydride with ethylene glycol, diethylene glycol, polyethylene glycol, propylene glycol, dipropylene glycol, polypropylene glycol, 1,4-butanediol, ethylenediamine or hexamethylenediamine in the presence of tertiary amine such as pyridine or triethylamine, subsequently preparing carboxylic chloride in the same manner as in the compound of Formula (1) and further reacting it with hydroxyperoxide.

Further, $R_5$, $R_7$, $R_8$, $R_9$, $R_{10}$ and $R_{11}$ are synonymous with $R_1$ and $R_2$ in Formula (1), and $X_3$ is synonymous with $X_1$ and $X_2$ in Formula (1). $R_6$ and $R_{12}$ are synonymous with $R_3$ and $R_4$ in Formula (1), and the same raw materials can be used to produce the respective compounds.

The compound represented by Formula (2) has a high sensitivity since it has a lot of peracid ester structures in a molecule. Further, the physical properties of the cured paint film can be controlled by adjusting the alkyl chain length, and therefore it is very useful.

Glycerin or triethanolamine may be reacted with the acid anhydride described above. In that case, the molar ratio is to be carefully controlled. If the molecular weight becomes extra high, handling may be difficult.

The photopolymerization initiator of the present invention thus obtained is inexpensive in terms of a production cost and has a high sensitivity. Precipitation of crystals does not take place during cold storage after being diluted and dissolved in a solvent. It has excellent characteristics as a component of a photopolymerizable initiator composition.

The photopolymerizable initiator composition can be obtained by blending and dissolving the photopolymerization initiator of the present invention, a binder polymer, a photopolymerizable monomer and a solvent. The photopolymerization initiator of the present invention, when used alone, has a low sensitivity to an i beam, an h beam and a g beam. Therefore when these beams are used, it is desirable to use the present photopolymerization initiator in combination with other photopolymerization initiators and/or sensitizing dyes.

Specific examples of said other photopolymerization initiators or sensitizing dyes include benzophenone, Michler's ketone, 4,4'-bis(diethylamino)benzophenone, xanthone, thioxanthone, isopropylxanthone, 2,4-diethylthioxanthone, 2-ethylanthraquinone, acetophenone, 2-hydroxy-2-ethylpropiophenone, 2-hydroxy-2-methyl-4'-isopropylpropiophenone, 1-hydroxycyclohexyl phenyl ketone, isopropyl benzoin ether, isobutyl benzoin ether, 2,2-diethoxyacetophenone, 2,2-dimethoxy-2-phenylacetophenone, benzil, camphorquinone, benzanthrone, 2-methyl-1-[4-(methylthio)phenyl]-2-morpholinopropane-1-one, 2-benzyl-2-dimethylamino-1-(4-morpholinophenyl)-butanone-1, ethyl 4-dimethylaminobenzoate, isoamyl 4-dimethylaminobenzoate, 4,4'-di(t-butyl peroxycarbonyl)benzophenone, 3,4,4'-tri(t-butyl peroxycarbonyl)benzophenone, 3,3',4,4'-tetra(t-butyl peroxycarbonyl)benzophenone, 3,3',4,4'-tetra(t-hexyl peroxycarbonyl)benzophenone, 2,4,6-trimethylbenzoyl-diphenylphosphine oxide, methyl 2,4,6-trimethylbenzoyl-phenylphosphinate, ethyl 2,4,6-trimethylbenzoyl-phenylphosphinate, 2,4-dichlorobenzoyl-diphenylphosphine oxide, 2,6-dichlorobenzoyl-diphenylphosphine oxide, 2,3,5,6-tetramethylbenzoyl-diphenylphosphine oxide, 3,4-dimethylbenzoyl-diphenylphosphine oxide, bis(2,4,6-trimethylbenzoyl)-phenylphosphine oxide, bis(2,6-dimethoxybenzoyl)-2,4,4-trimethyl-pentylphosphine oxide, 4-[p-N,N-di(ethoxycarbonylmethyl)]-2,6-di(trichloromethyl)-s-triazine, 1,3-bis(trichloromethyl)-5-(2'-chlorophenyl)-s-triazine, 1,3-bis(trichloromethyl)-5-(4'-methoxyphenyl)-s-triazine, 2-(p-dimethylaminostyryl)benzoxazole, 2-(p-dimethylaminostyryl)benzothiazole, and 3,3'-carbonylbis( 7-diethylaminocoumarin). It is also effective to use them in a mixture of two or more thereof.

Among the above-mentioned, preferred are 4,4'-bis(diethylamino)benzophenone, 2-methyl-1-[4-(methylthio)phenyl]-2-morpholinopropane-1-one and 2-benzyl-2-dimethylamino-1-(4-morpholinophenyl)-butanone-1. Particularly preferred is the case where 4,4'-bis(diethylamino)benzophenone and 2-benzyl-2-dimethylamino-1-(4-morpholinophenyl)-butanone-1 are used in combination or the case where 4,4'-bis(diethylamino)benzophenone, 2-benzyl-2-dimethylamino-1-(4-morpholinophenyl)-butanone-1 and 2-methyl-1-[4-(methylthio)phenyl]-2-morpholinopropane-1-one are used in combination, because the sensitivity, the compatibility with a resin and the storage stability are high, and the pattern edge form is good as well.

The blending proportion of the photopolymerization initiator and the sensitizing dye in the photopolymerizable initiator composition of the present invention is preferably 2 to 100% in terms of the total of the photopolymerization initiator and the sensitizing dye based on the total amount of the binder polymer and the photopolymerizable monomer. If it is lower than 2%, the practical sensitivity can not be obtained, and if it exceeds 100%, the sensitivity reaches the uppermost limit, and the cost is rather increased.

The binder polymer usable for the photopolymerizable initiator composition of the present invention include, but not restricted thereto, (meth)acrylic resins, polyesters, polyimides, polystyrenes, epoxy resins, styrene-maleic anhydride copolymers, butyral resins, polyvinyl chloride, polyvinyl acetate, polyvinyl formal, polyvinyl alcohol, polyamides, phenol resins, polyurethane, cellulose base polymers, polyvinylpyrrolidone, polyethylene glycol, polypropylene glycol, polyethyleneimine, melamine resins, guanamine resins, polyethylene and polypropylene.

In these years, a demand for a high function photopolymerizable initiator composition capable of removing an unexposed part with an alkali solution to provide optional patterns has been increased. Suitable for this use are (meth)acrylic resins, styrene-maleic anhydride copolymers, polyvinyl alcohol, phenol resins, polyvinylpyrrolidone, polyethylene glycol and polypropylene glycol. Particularly suitable are (meth)acrylic resins and styrene-maleic anhydride copolymers with which the alkali developing characteristics are easily controlled. The blending proportion of the binder polymer is preferably 1 to 70% based on the whole amount of the photopolymerization initiator composition, but it may be without this range, for example, no binder polymer used, depending on uses.

The photopolymerizable monomer used for the photopolymerizable initiator composition of the present invention includes, but not restricted thereto, monofunctional monomers such as (meth)acrylic acid, 2-hydroxyethyl (meth)acrylate, 2-hydroxypropyl (meth)acrylate, 4-hydroxybutyl (meth)acrylate, methyl (meth)acrylate, ethyl (meth)acrylate, isopropyl (meth)acrylate, n-butyl (meth)acrylate, isobutyl (meth)acrylate, t-butyl (meth)acrylate, 2-ethylhexyl (meth)acrylate, hexyl (meth)acrylate, cyclohexyl (meth)acrylate, octyl (meth)acrylate, tridecyl (meth)acrylate, lauryl (meth)acrylate, stearyl (meth)acrylate, phenyl (meth)acrylate, benzyl (meth)acrylate, 2-methoxyethyl (meth)acrylate, ethoxyethoxyethyl (meth)acrylate, 3-methoxybutyl (meth)acrylate, phenoxyethyl (meth)acrylate, cetyl (meth)acrylate, isobornyl (meth)acrylate, dimethylaminoethyl (meth)acrylate, dimethylaminoethyl (meth)acrylate-quaternized product, morpholinoethyl (meth)acrylate, trimethylsiloxyethyl (meth)acrylate, Biscoat #193, Biscoat #320, Biscoat #2311HP, Biscoat #220, Biscoat #2000, Biscoat #2100, Biscoat #2150, Biscoat #2180, Biscoat 3F, Biscoat 3FM, Biscoat 4F, Biscoat 4FM, Biscoat 6FM, Biscoat 8F, Biscoat 8FM, Biscoat 17F, Biscoat 17FM and Biscoat MTG each manufactured by Osaka Organic Chemistry Co., Ltd., M-101, M-102, M-110, M-113, M-117, M-120, M-5300, M-5600, M-5700, TO-850, TO-851, TO-1248, TO-1249, TO-1301, TO-1317, TO-1315, TO-981, TO-1215, TO-1316, TO-1322, TO-1342, TO-1340 and TO-1225 each manufactured by Toa Gosei Co., Ltd., (2-mono(meth)acryloyloxy)ethyl cyclohexene-3,4-dicarboxylate, 3-cyclohexenylmethyl (meth)acrylate, 2-tetrahydrophthalimidethyl (meth)acrylate, (meth)acrylamide, dimethylaminopropyl(meth)acrylamide, N,N-dimethylacrylamide, styrene, α-methylstyrene, maleic anhydride, N-vinylpyrrolidone and 4-acryloylmorpholine, and multifunctional monomers such as trimethylolpropane tri(meth)acrylate, pentaerythritol tri(meth)acrylate, pentaerythritol tetra(meth)acrylate, dipentaerythritol penta(meth)acrylate, dipentaerythritol hexa(meth)acrylate, tris(meth)acryloyloxyethyl phosphate, polyethylene glycol di(meth)acrylate, isocyanuric acid ethylene oxide-modified tri(meth)acrylate, isocyanuric acid ethylene oxide-modified di(meth)acrylate, polyester (meth)acrylate and diglycerin tetra(meth)acrylate. It is a matter of course that two or more of the monomers can be used in a mixture.

Among these monomers, pentaerythritol triacrylate, pentaerythritol tetraacrylate, dipentaerythritol pentaacrylate and dipentaerythritol hexaacrylate have a high sensitivity and therefore are preferred. In particular, dipentaerythritol pentaacrylate and dipentaerythritol hexaacrylate have a good spattering resistance on the paint film surface after curing by photopolymerization and therefore are more preferred.

In uses of a high function photopolymerizable initiator composition in which the unexposed part can be removed with an alkali solution to provide optional patterns, it is effective for controlling the form of the pattern edges to blend and use monofunctional monomers and difunctional monomers such as polyethylene glycol diacrylate, polypropylene glycol diacrylate, ethylene glycol phthalate acrylate, and KAYARAD TC-110S, KAYARAD R-712, KAYARAD R-551 and KAYARAD R-684 each manufactured by Nippon Kayaku Co., Ltd.

The blending proportion of the photopolymerizable monomer shall not specifically be restricted and is usually 1 to 90% based on the whole amount of the photopolymerizable initiator composition.

The solvent used for the photopolymerizable initiator composition of the present invention shall not specifically be restricted as long as it dissolves the photopolymerization initiator, the binder monomer and the photopolymerizable monomer, and there can be used, for example, water, ethanol, 2-propanol, 2-butanone, ethyl acetate, butyl acetate, ethylene glycol monoisopropyl ether, ethylene glycol monobutyl ether, ethyl carbitol, propylene glycol monomethyl ether, propylene glycol monomethyl ether acetate, ethylene glycol monobutyl ether acetate, cyclohexanone, cyclopentanone, diethylene glycol dimethyl ether, diethylene glycol diethyl ether, toluene, xylene, γ-butyrolactone and N,N-dimethylacetamide.

Among these solvents, propylene glycol monomethyl ether, propylene glycol monomethyl ether acetate, cyclohexanone and toluene are more preferred in terms of the uniformity of the film thickness in coating. It is a matter of course that they can be used in the form of a mixed solvent of two or more thereof. A non-solvent type photopolymerizable initiator composition using no solvents is preferred from the viewpoint of influence on the environment.

Adding a silane coupling agent, a leveling agent, a surfactant, an adhesive and the like to the photopolymerizable initiator composition of the present invention is effective for enhancing the various characteristics of the composition. Blending of a coloring material with the photopolymerizable initiator composition can provide a photosensitive colored composition.

Specific examples of the coloring material include synthetic dyes such as azo dyes, anthraquinone dyes, triphenylmethane dyes, polymethine dyes, metal complex salt dyes, bisazo dyes, trisazo dyes, sulfur dyes and indigo dyes, and organic pigments such as C. I. Pigment Yellow 12, 13, 14, 17, 20, 24, 31, 55, 83, 93, 109, 110, 137, 139, 150, 153, 154, 166, 168 and 173, C. I. Pigment Orange 36, 43 and 51, C. I. Pigment Red 9, 97, 122, 123, 149, 176, 177, 180, 215 and 254, C. I. Pigment Violet 19, 23 and 29, C. I. Pigment Blue 15, 15:3 and 15:6, C. I. Pigment Green 7 and 36, C. I. Pigment Brown 28 and C. I. Pigment Black 1 and 7.

In a photosensitive colored composition for color filters for which demand has increased in recent years, organic pigments are preferably used in terms of the heat resistance and the light fastness. C. I. Pigment Red 177 and 254, C. I. Pigment Yellow 139 and 150, C. I. Pigment Green 36 and C. I. Pigment Blue 15 and 15:6 are particularly preferred from the viewpoints of color purity and transmission. The blending proportion of these coloring materials shall not specifically be restricted and is usually 1 to 50% base on the whole amount of the photosensitive colored composition.

EXAMPLES

The present invention shall further be explained below with reference to examples.

Example 1

50 g of 3,3',4,4'-benzophenonetetra-carboxylic dianhydride, 25 g of pyridine, 20 g of methanol and 100 g of toluene were mixed and reacted at 80° C. for 10 hours. Excess methanol was distilled off, and then 60 g of thionyl chloride was slowly dropwise added at 30° C. After finishing dropwise adding, the solution was stirred at 30° C. for one hour, and it was further heated to 50° C. and stirred for 2 hours. After finishing the reaction, unreacted thionyl chloride and toluene were removed under reduced pressure to obtain a crude acid chloride. The residue was dissolved again in toluene and washed once with water, and then the organic layer was separated. After drying this on anhydrous sodium sulfate, the desicating agent was filtered off, and the resulting solution was condensed under reduced pressure to obtain a pale yellow viscous acid chloride. A chart of proton NMR of this compound using tetramethylsilane as a reference material was shown in FIG. 1. According to this chart, it is apparent from an intensity ratio 6.000/6.135= 6/6 of a peak based on hydrogen atoms of a benzene ring in about 8 ppm to a peak based on hydrogen atoms of a methyl group in about 4 ppm that this is the desired compound. A peak in the vicinity of 7.5 ppm and a peak in 3 ppm are peaks based on toluene which is the reaction solvent. Next, 100 g of a 10% toluene solution of t-butyl hydroperoxide and 10 g of triethylamine were blended and cooled, and a toluene solution of the acid chloride described above was slowly dropwise added to carry out dehydrochlorination reaction. After finishing dropwise adding, the solution was stirred at 5° C. for one hour and subsequently at a room temperature for 3 hours. After removing triethylamine hydrochloride by filtering, the solution was washed twice with water and dried on anhydrous sodium sulfate. Then, toluene was distilled off under reduced pressure to obtain 42 g of a 25% toluene solution of a photopolymerization initiator having the structure shown below. The concentration of the photopolymerization initiator was determined from loss on drying. There may be included the case where t-butyl hydroperoxide groups and methoxy groups connected to four carbonyl groups which are connected to 3-, 3'-, 4- and 4'-positions are replaced with each other between the 3-position and 4-position and the 3'-position and 4'-position.

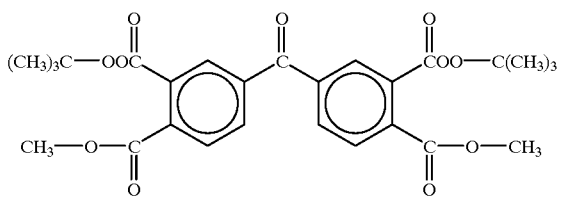

A 25% toluene solution of this photopolymerization initiator was stored at 5° C. for 3 months, but no precipitation of crystals was observed.

Comparative Example 1

A 25% toluene solution of 3,3',4,4'-tetra(t-butylperoxycarbonyl)benzophenone was stored at 5° C. for 3 months, and precipitation of crystals was observed.

Example 2

50 g of 3,3',4,4'-benzophenonetetracarboxylic dianhydride, 25 g of pyridine, 9 g of ethylene glycol and 100 g of toluene were mixed and reacted at 80° C. for 10 hours. The solution was cooled down to 30° C., and then 60 g of thionyl chloride was slowly dropwise added. After finishing the dropwise addition, the solution was stirred at 30° C. for one hour, and it was further heated to 50° C. and stirred for 2 hours. After finishing the reaction, unreacted thionyl chloride and toluene were removed under reduced pressure to obtain a crude acid chloride. The residue was dissolved again in toluene and washed once with water, and then the organic layer was separated. After drying this on anhydrous sodium sulfate, the desicating agent was filtered off, and the resulting solution was condensed under reduced pressure to obtain a pale yellow viscous acid chloride. This was reacted with t-butyl hydroperoxide by the same method as in Example 1 to obtain a 25% toluene solution of a photopolymerization initiator corresponding to Formula (2). This was stored at 5° C. for 3 months, but no precipitation of crystals was observed.

Examples 3 to 9

Photopolymerization initiators were synthesized in the same molar ratio of the respective reagents as in Example 1, except that methanol used in Example 1 was changed to ethanol, n-butylamine, 1-butanol, benzyl alcohol, 2-hydroxyethyl acrylate, hydroxybutyl acrylate and tetrahydrofurfuryl alcohol. 25% toluene solutions of these photopolymerization initiators were stored at 5° C. for 3 months, but no precipitation of crystals was observed.

Example 10

A photopolymerization initiator was synthesized in the same mole ratio of the respective reagents as in Example 1, except that t-butyl hydroperoxide used in Example 1 was changed to t-hexyl hydroperoxide. A 25% toluene solution of this photopolymerization initiator was stored at 5° C. for 3 months, but no precipitation of crystals was observed.

Example 11

0.50 g of a benzyl methacrylate/methyl methacrylate/2-hydroxyethyl methacrylate/methacrylic acid quaternary copolymer (molar ratio 46:16:13:25, weight-average molecular weight: 7,000 which was determined by GPC using polyethylene oxides as a reference), 2.00 g of propylene glycol monomethyl ether acetate, 0.40 g of M-400 manufactured by Toa Gosei Co., Ltd., 0.10 g of M-240 manufactured by Toa Gosei Co., Ltd., 0.05 g of 4,4'-bis(diethylamino)benzophenone, 0.20 g of a 25% toluene solution of the photopolymerization initiator synthesized in Example 1 and 0.002 g of BYK-300 manufactured by Bic Chemie Japan Co., Ltd. were mixed and then stirred to obtain a photopolymerizable initiator composition.

The photopolymerizable initiator composition was spin-coated on a glass substrate at 1200 rpm for 5 seconds and dried on a hot plate at 90° C. for one minute, wherein the film thickness was 1.36 μm. This substrate was exposed to a UI-501C ultra-high pressure mercury lamp manufactured by Ushio Co., Ltd. in the air at a gap of 100 μm via a mask of a stripe pattern of 20 μm. The exposure was measured by means of an integrating luminous energy meter UIT-102 and a light receiving device UVD-365PD each manufactured by Ushio Co., Ltd. The glass substrate after exposure was subjected to shower development in a developing solution obtained by dissolving 5 g of sodium hydrogencarbonate and 2.5 g of sodium carbonate in 5000 g of demineralized water to remove an unexposed part, and the film thickness of the resulting pattern was measured. The exposure in which the film thickness was saturated was 15 mj, wherein the film thickness was 1.31 μm.

Example 12

The photopolymerization initiator synthesized in Example 2 was used to prepare a photopolymerizable initiator composition in the same manner as in Example 11. The film thickness before exposure was 1.40 μm, and the exposure in which the film thickness was saturated was 10 mj, wherein the film thickness was 1.36 μm.

Example 13

Solspars 5 g manufactured by Zeneca Co., Ltd. was dissolved in 20 g of propylene glycol monomethyl ether acetate, and 12 g of C. I. Pigment Red 254 and 3 g of C. I. Pigment Yellow 139 were added thereto. The mixture was kneaded by means of a three-roll mill, and then 60 g of propylene glycol monomethyl ether acetate and 400 g of zirconia beads having a diameter of 0.5 mm were added, followed by stirring it by means of a sand mill for 20 hours. This solution was filtered through a Teflon-made membrane filter having a pore diameter of 1 μm to obtain 95 g of a red dispersion.

The whole amount of the photopolymerizable initiator composition prepared in Example 12 was slowly dropwise added to 2 g of the red dispersion while stirring to obtain a red photosensitive colored composition. This was evaluated in the same manner as in Example 11. The film thickness before exposure was 1.29 μm, and the exposure in which the film thickness was saturated was 25 mj, wherein the film thickness was 1.23 μm. The resulting pattern was post-baked at 200° C. for 10 minutes and then heated at 250° C. for one hour to observe a change in the color to find that ΔE was 0.31 and the heat resistance was good.

Comparative Example 2

A 25% toluene solution of 3,3',4,4'-tetra(t-butyl peroxycarbonyl)benzophenone was used to prepare a photopolymerizable initiator composition in the same manner as in Example 11. Further, a photosensitive colored composition was prepared and evaluated in the same manner as in Example 13. The film thickness before exposure was 1.28 μm, and the exposure in which the film thickness was saturated was 45 mj, wherein the film thickness was 1.21 μm. ΔE was 0.30, and the heat resistance was good.

According to the present invention, an inexpensive photopolymerization initiator having a high sensitivity and a high storage stability can be obtained. A photopolymerizable initiator composition using this photopolymerization initiator has a high sensitivity. Further, a photosensitive colored composition obtained by further mixing a coloring material such as a pigment shows as well a high sensitivity and a high heat resistance and shows excellent characteristics as a material for producing a color filter.

What is claimed is:

1. A photopolymerization initiator represented by the following Formula (1):

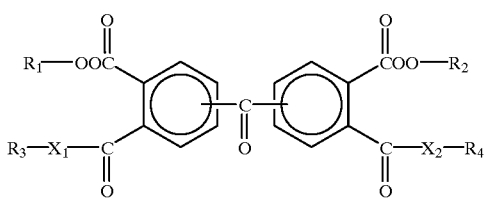
(1)

wherein $R_1$ and $R_2$ represents independently a tertiary alkyl group having 4 to 15 carbon atoms or a tertiary aralkyl group having 9 to 15 carbon atoms; $-X_1-R_3$ and $-X_2-R_4$ represents independently an alkoxy group which is an alcohol residue of methanol, ethonal, 2-propanal, 1-butanol, benzyl alcohol, dimethylaminoethanol, diethylaminoethanol, tetrahydrofurfuryl alcohol or a monoalcohol obtained by adding tetrahydrofurfuryl alcohol to ε-caprolactone.

2. The photopolymerization initiator according to claim 1, wherein $-X_1-R_3$ and $-X_2-R_4$ in Formula (1) represent independently an alkoxy group which is an alcohol residue of methanol, ethanol, 2-propanol, 1-butanol or benzyl alcohol.

3. The photopolymerization initiator according to claim 1, wherein $-X_1-R_3$ and $-X_2-R_4$ in Formula (1) represent independently an alkoxy group which is an alcohol residue of dimethylaminoethanol or diethylaminoethanol.

4. The photopolymerization initiator according to claim 1, wherein $-X_1-R_3$ and $-X_2-R_4$ in Formula (1) represent independently an alkoxy group which is an alcohol residue of tetrahydrofurfuryl alcohol or monoalcohol obtained by adding tetrahydrofurfuryl alcohol to ε-caprolactone.

5. A photopolymerization initiator represented by the following Formula (2):

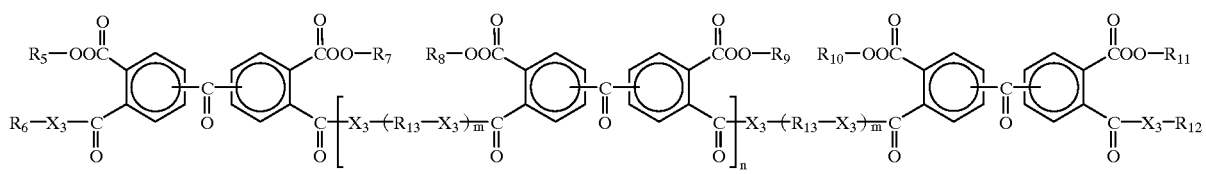
(2)

wherein $R_5$, $R_7$, $R_8$, $R_9$, $R_{10}$ and $R_{11}$ represent independently a tertiary alkyl group having 4 to 15 carbon atoms or a tertiary aralkyl group having 9 to 15 carbon atoms; $R_6$ and $R_{12}$ represent independently a tertiary alkoxy group having 4 to 15 carbon atoms, a tertiary aralkyloxy group having 9 to 15 carbon atoms or an organic group having 1 to 30 carbon atoms in which an atom bonded to $X_3$ is not an oxygen atom; $X_3$ represents —O— or —NH—; $R_{13}$ represents an alkylene group having 2 to 8 carbon atoms; m represents an integer of 1 to 30; and n represents an integer of 0 to 30.

6. The photopolymerization initiator according to claim 5, wherein $-X_3-R_6$ and $-X_3-R_{12}$ in Formula (2) represent independently an alkoxy group which is an alcohol residue of methanol, ethanol, 2-propanol, 1-butanol or benzyl alcohol.

7. The photopolymerization initiator according to claim 5, wherein $-X_3-R_6$ and $-X_3-R_{12}$ in Formula (2) represent independently an alkoxy group which is an alcohol residue of 2-hydroxyethyl (meth)acrylate, 2-hydroxyproyl (meth)acrylate, polyethylene glycol mono(meth)acrylate, polypropylene glycol mono(meth)acrylate or hydroxybutyl (meth)acrylate.

8. The photopolymerization initiator according to claim 5, wherein $-X_3-R_6$ and $-X_3-R_{12}$ in Formula (2) represent independently an alkoxy group which is an alcohol residue of dimethylaminoethanol or diethylaminoethanol.

9. The photopolymerization initiator according to claim 5, wherein $-X_3-R_6$ and $-X_3-R_{12}$ in Formula (2) represent independently an alkoxy group which is an alcohol residue of tetrahydrofurfuryl alcohol or monoalcohol obtained by adding tetrahydrofurfuryl alcohol to ε-caprolactone.

10. A photopolymerizable initiator composition comprising at least one photopolymerization initiator represented by Formula (1)

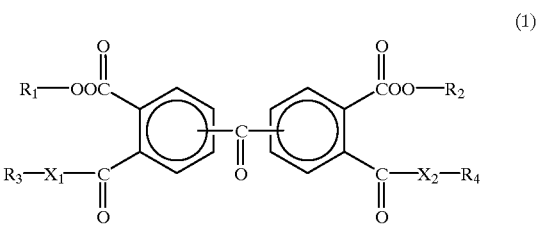
(1)

wherein $R_1$ and $R_2$ represent independently a tertiary alkyl group having 4 to 15 carbon having 9 to 15 carbon atoms; $-X_1-R_3$ and $-X_2-R_4$ represent independently an alkoxy group which is an alcohol residue of methanol, ethanol, 2-propanol, 1-butanol, benzyl alcohol, dimethylaminoethanol, diethylaminoethanol, tetrahydrofurfuryl alcohol or a monoalcohol obtained by adding tetrahydrofurfuryl alcohol to ε-caprolactone; or of the following formula (2):

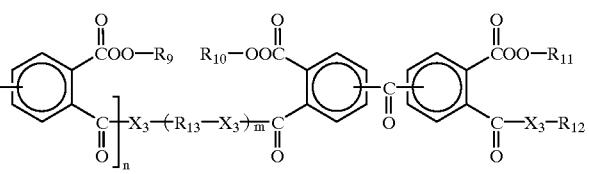

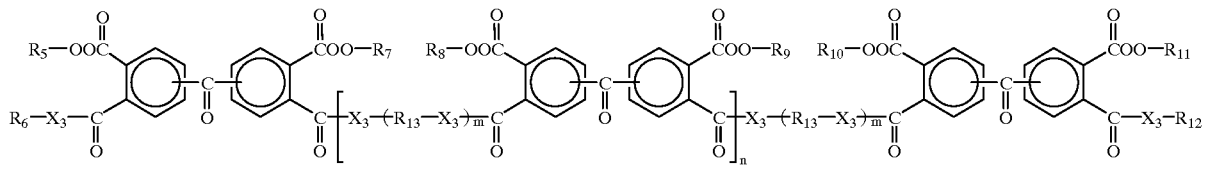

(2)

wherein $R_5$, $R_7$, $R_8$, $R_9$, $R_{10}$ and $R_{11}$ represent independently a tertiary alkyl group having 4 to 15 carbon atoms or a tertiary aralkyl group having 9 to 15 carbon atoms; $R_6$ and $R_{12}$ represent independently a tertiary alkoxy group having 4 to 15 carbon atoms, a tertiary aralkyloxy group having 9 to 15 carbon atoms or an organic group having 1 to 30 carbon atoms in which an atom bonded to $X_3$ is not an oxygen atom; $X_3$ represents —O— or —NH—; $R_{13}$ represents an alkylene group having 2 to 8 carbon atoms, m represents an integer of 1 to 30; and n represents an integer of 0 to 30.

11. The photopolymerizable initiator composition according to claim 10, wherein at least one photopolymerization initiator other than those represented by Formulas (1) and (2) and/or one sensitizing dye is used in an amount of 1 to 80% by weight based on the total amount of the photopolymerization initiators and the sensitizing dye.

12. A photosensitive colored composition comprising the photopolymerizable initiator composition as claimed in claim 10 in admixture with a coloring material.

13. A color filter produced by using the photosensitive colored composition as claimed in claim 12.

14. A liquid crystal display element produced by using the color filter as claimed in claim 13.

* * * * *

UNITED STATES PATENT AND TRADEMARK OFFICE
CERTIFICATE OF CORRECTION

PATENT NO.   : 6,344,299 B1
DATED        : February 5, 2002
INVENTOR(S)  : Hiroyuki Sato et al.

It is certified that error appears in the above-identified patent and that said Letters Patent is hereby corrected as shown below:

Column 11,
Line 29, replace "represents" with -- represent --
Line 30, replace "ethonal" with -- ethanol --
Line 30, replace "propanal" with -- propanol --

Column 12,
Line 47, after "4 to 15 carbon" insert -- atoms or a tertiary aralkyl group --
Line 64, replace "ftiryl" with -- furyl --

Signed and Sealed this

Twenty-third Day of April, 2002

Attest:

Attesting Officer

JAMES E. ROGAN
*Director of the United States Patent and Trademark Office*